United States Patent [19]

Kühle et al.

[11] Patent Number: 4,459,151
[45] Date of Patent: Jul. 10, 1984

[54] HERBICIDALLY ACTIVE FLUORINE-CONTAINING 4,6-DIAMINO-S-TRIAZINES

[75] Inventors: Engelbert Kühle, Bergisch-Gladbach; Bernd Baasner, Leverkusen; Hermann Hagemann, Leverkusen; Ludwig Eue, Leverkusen; Robert R. Schmidt, Bergisch-Gladbach, all of Fed. Rep. of Germany

[73] Assignee: Bayer Aktiengesellschaft, Leverkusen, Fed. Rep. of Germany

[21] Appl. No.: 408,082

[22] Filed: Aug. 13, 1982

[30] Foreign Application Priority Data

Aug. 29, 1981 [DE] Fed. Rep. of Germany ....... 3134227
May 19, 1982 [DE] Fed. Rep. of Germany ....... 3218966

[51] Int. Cl.³ .................. C07D 251/50; C07D 251/52; C07D 251/66; A01N 43/70
[52] U.S. Cl. ........................................ 71/93; 544/197; 544/204
[58] Field of Search ..................... 544/204, 197; 71/93

[56] References Cited

U.S. PATENT DOCUMENTS 3,419,556 12/1968 Schubert et al. ..................... 544/204
3,494,759 2/1970 Mason et al. ......................... 544/204

FOREIGN PATENT DOCUMENTS 674325 11/1963 Canada ................................. 544/204
1770576 11/1971 Fed. Rep. of Germany .
2141394 2/1972 Fed. Rep. of Germany .
1695117 3/1972 Fed. Rep. of Germany .
2425287 12/1975 Fed. Rep. of Germany .
336223 3/1959 Switzerland .
428750 7/1967 Switzerland .

OTHER PUBLICATIONS

Chemie der Pflanzenschutz–und Schädlings–bekämpfungsmittel, vol. 5, 1977, pp. 336 to 352.

*Primary Examiner*—John M. Ford
*Attorney, Agent, or Firm*—Sprung, Horn, Kramer & Woods

[57] ABSTRACT

Fluorine-containing 4,6-diamino-s-triazines of the formula

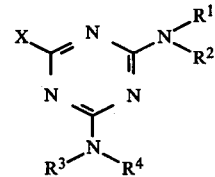

wherein
X is a chlorine atom, an alkoxy radical having 1 to 4 carbon atoms, an alkylthio radical having 1 to 4 carbon atoms or the azide radical,
$R^1$, $R^2$ and $R^3$ each independently is a hydrogen atom or an aliphatic radical, and
$R^4$ is a fluoroalkyl or fluorochloroalkyl radical, which possess herbicidal activity. Intermediates wherein X is chlorine and $-NR^1R^2$ is replaced by chlorine are also new.

9 Claims, No Drawings

HERBICIDALLY ACTIVE FLUORINE-CONTAINING 4,6-DIAMINO-S-TRIAZINES

The present invention relates to certain new fluorine-containing s-triazine derivatives, to a process for their production, to their use as herbicides and to intermediate products for their preparation.

It has already been known for a long time that certain s-triazine derivatives can be employed as herbicides. 2-Chloro-4-ethylamino-6-isopropylamino-s-triazine (atrazine), for example, has become particularly important in practice, and can be used, as is known, for combating weeds in corn crops (see, for example, "Chemie der Pflanzenschutz- und Schädlingsbekämpfungsmittel" (Chemistry of Plant Protection Agents and Pest-combating Agents), Volume 5—Herbicides, published by R. Wegler, Springer-Verlag Berlin Heidelberg, New York, 1977, pages 336–352).

However, atrazine is ineffective or not completely effective against grasses of the millet species for example, Echinochloa, Digitaria and Setaria.

The present invention now provides, as new compounds, the fluorine-containing 4,6-diamino-s-triazines of the general formula

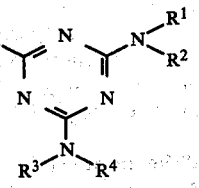
(I)

wherein
X represents a chlorine atom, an alkoxy radical having 1 to 4 carbon atoms, an alkylthio radical having 1 to 4 carbon atoms or the azide radical (—N$_3$),
R$^1$, R$^2$ and R$^3$ are identical or different and represent a hydrogen atom or a saturated or unsaturated aliphatic radical, and
R$^4$ represents a fluoroalkyl or fluorochloroalkyl radical.

According to the present invention we provide a process for the production of a compound of the present invention, characterized in that, in a first stage a 2,4-dichloro-6-(fluoroalkylamino)-s-triazine of the general formula

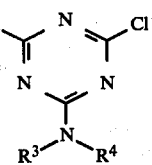
(II)

wherein
R$^3$ and R$^4$ have the meanings given above, is reacted with an amine of the general formula

(III)

wherein
R$^1$ and R$^2$ have the meanings given above, in the presence of an acid-binding agent and, if appropriate, in the presence of a diluent and, in a second stage, if a compound of formula (I) is required in which X does not represent a chlorine atom, the resulting 2-chloro-4,6-diamino-s-triazine of the general formula

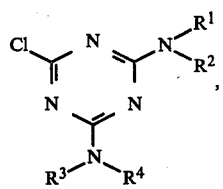
(Ia)

wherein
R$^1$, R$^2$, R$^3$ and R$^4$ have the meanings given above, is reacted with a C$_1$ to C$_4$ alcohol, with a C$_1$ to C$_4$ mercaptan or with hydrazoic acid (HN$_3$), in each case in the form of a salt or in the presence of an acid-binding agent, and if appropriate in the presence of a diluent, a substituted 4,6-diamino-s-triazine of the formula

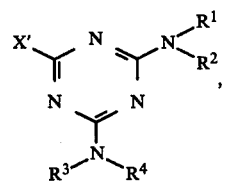
(Ib)

wherein
X' represents an alkoxy or alkylthio radical, each having 1 to 4 carbon atoms, or the azide radical, and R$^1$, R$^2$, R$^3$ and R$^4$ have the meanings given above, being obtained.

In addition, it has been found that the new fluorine-containing s-triazine derivatives of the present invention of formula (I) have powerful herbicidal properties.

Surprisingly, the active compounds according to the invention have a better selective action and a broader spectrum of action than the previously known triazines. In particular, it has been found that the active compounds according to the invention are considerably more effective than the previously known atrazine against grasses of the millet species.

Preferred compounds of formula (I) according to the present invention are those
in which
X represents a chlorine atom, an alkoxy radical having 1 to 4 carbon atoms, an alkylthio radical having 1 to 4 carbon atoms or the azide radical,
R$^1$, R$^2$ and R$^3$ each independently of one another represent a hydrogen atom, an alkyl radical having 1 to 6 carbon atoms or an alkenyl radical having 3 to 6 carbon atoms, and
R$^4$ represents a fluoroalkyl radical having 1 to 8 carbon atoms and 1 to 9 fluorine atoms, or a fluorochloroalkyl radical having 1 to 8 carbon atoms and up to a total of 9 fluorine and chlorine atoms. Further, R$^2$ can also represent one of the following aliphatic radicals: ethylthioethyl, methoxyethyl, 2-chloroethyl, 2-hydroxyethyl, ethoxycarbonylmethyl.

If, for example, 2,4-dichloro-6-(1-methyl-2,2,2-trifluoroethylamino)-s-triazine and ethylamine are used, according to process A, as starting materials, and the resulting 2-chloro-4-ethylamino-6-(1-methyl-2,2,2-trifluoroethylamino)-s-triazine is reacted further with sodium methanolate, the course of the reaction according to the present invention for the production of formula (I) is illustrated by the following equation:

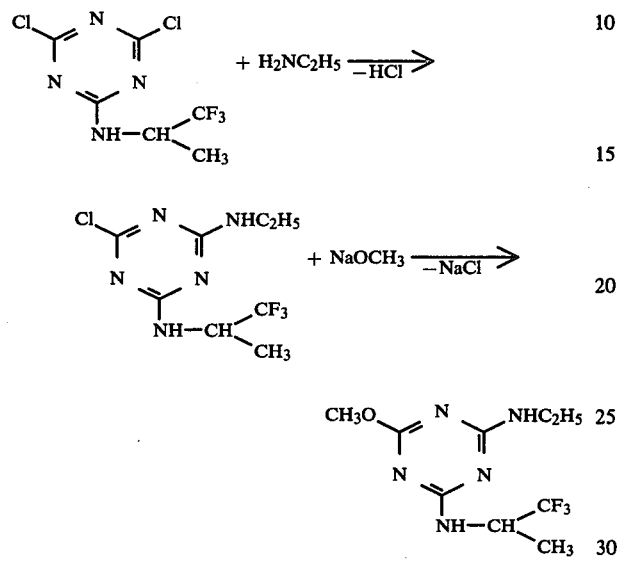

The 2,4-dichloro-6-(fluoro-alkylamino)-s-triazines of the formula (II) used as starting compounds for the production of compounds of formula (I), are themselves novel and form a further subject of the present invention.

According to the present invention we further provide a process for the production of a compound of formula (II), characterized in that cyanuric chloride of the formula

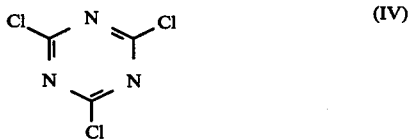

(IV)

is reacted with a fluorine-containing primary or secondary amine of the general formula

(V)

wherein
R$^3$ and R$^4$ have the meanings given above, in the presence of an acid-binding agent and if appropriate in the presence of a diluent.

If cyanuric chloride and, for example, 1-methyl-2,2,2-trifluoro-ethylamine are used as starting materials, the course of the reaction according to the present invention for the production of a compound of formula (II) is illustrated by the following equation:

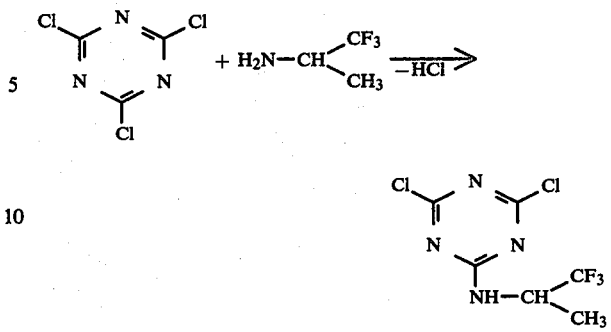

Preferred compounds of formulae (V) or (II) are those in which
R$^3$ represents a hydrogen atom, an alkyl group having 1 to 6 carbon atoms or an alkenyl group having 3 to 6 carbon atoms, and
R$^4$ represents a straight-chain or branched fluoroalkyl group having 1 to 8 carbon atoms and 1 to 9 fluorine atoms, or a straight-chain or branched fluorochloroalkyl group having 1 to 8 carbon atoms and up to a total of 9 fluorine and chlorine atoms.

Particularly preferred compounds of the formulae (V) or (II) are those in which R$^4$ represents a straight-chain or branched fluoroalkyl group having 1 to 6 carbon atoms and 1 to 7 fluorine atoms, or a straight-chain or branched fluorochloroalkyl group having 1 to 6 carbon atoms and up to a total of 7 fluorine and chlorine atoms.

Compounds of the formula (V) or (II) may be specifically mentioned are those in which R$^4$ represents a 2,2,2-trifluoroethyl, pentafluoroethyl, 3,3,3-trifluoropropyl, 2,2,2-trifluoro-1-methyl-ethyl, 4,4,4-trifluoro-n-butyl, 1-(trifluoromethyl)-n-propyl, 1-(trifluoromethyl)-n-butyl, 1-(trifluoromethyl)-n-pentyl, 1-(trifluoromethyl)-2-methylpropyl, 3-fluoro-3,3-dichloro-n-propyl, 3-fluoro-3-chloro-n-propyl, 2,2-difluoropropyl or 2,3,3,3-tetrafluoro-2-chloro-propyl radical.

Preferred amines of formula (III) further to be used as starting compounds for the production of compounds of formula (I) are those in which
R$^1$ and R$^2$ represent a hydrogen atom or an alkyl group having 1 to 6 carbon atoms or an alkenyl group having 3 to 6 carbon atoms. Further, R$^2$ can also represent one of the following aliphatic radicals: ethylthioethyl, methoxyethyl, 2-chloroethyl, 2-hydroxyethyl, ethoxycarbonylmethyl.

The amines of the formula (III) are known. Suitable representatives are ammonia, methylamine, ethylamine, n-propylamine, isopropylamine, n-butylamine, isobutylamine, tert.-butylamine, hexylamine, allylamine, diethylamine, diallylamine and dibutylamine.

To prepare s-triazines of the formula (Ib), the s-triazines of the formula (Ia) are reacted with a C$_{1-4}$-alcohol or a C$_{1-4}$-mercaptan or with hydrazoic acid. In the formula (Ib), R$^1$, R$^2$, R$^3$ and R$^4$ have the meanings which have already been given as being preferred. Examples of suitable C$_{1-4}$-alcohols are methanol, ethanol, n-propanol, n-butanol and iso-butanol. Examples of suitable C$_{1-4}$-mercaptans are methylmercaptan, ethylmercaptan, n-propylmercaptan, isopropylmercaptan and n-butylmercaptan. Suitable salts of the alcohols and mercaptans mentioned are preferably the alkali metal salts, in particular the sodium salts.

Fluorine-containing amines of the formula (V) to be employed in the process for the production of compounds of formula (II) are known (see J. Org. Chem. 24, pages 1256–1259 (1959); J. Chem. Soc. 1954, pages 366–374; J. Org. Chem. 27, pages 1406–1409 (1962); J. Med. Chem. 22, pages 1130–1133 (1979); Izvest. Akad. Nauk. SSSR Ser. Khim. 1966, pages 1518–1923 (English version); U.S. Pat. No. 3,908,012; U.S. Pat. No. 3,960,949 and German Published Specification DOS 2,117,015. They can be prepared by methods which are known in principle.

Thus, for example, those fluorinated amines of the general formula

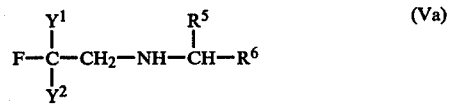

in which
Y$^1$ represents a hydrogen, fluorine or chlorine atom,
Y$^2$ represents a hydrogen, fluorine or chlorine atom,
R$^5$ represents an alkyl group and
R$^6$ represents a hydrogen atom or an alkyl group, are obtained by a process in which a fluorinated azomethine of the general formula

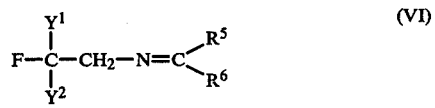

in which
Y$^1$, Y$^2$, R$^5$ and R$^6$ have the meanings given above, is hydrogenated with hydrogen under a pressure of 3 to 15 bar in the presence of a catalyst (such as platinum on charcoal, palladium on charcoal or Raney nickel) and in the presence of a diluent (for example an alcohol, such as methanol or ethanol, or an ether, such as dioxane) at a temperature between 0° C. and 60° C., preferably between 10° C. and 50° C.

Preferred compounds of formula (VI), are those in which
Y$^1$ represents a hydrogen, fluorine or chlorine atom,
Y$^2$ represents a hydrogen, fluorine or chlorine atom,
R$^5$ represents an alkyl group having 1 to 4 carbon atoms, and
R$^6$ represents a hydrogen atom or an alkyl group having 1 to 4 carbon atoms.

The azomethines of the formula (VI) required as starting materials in the preparation of the fluorinated amines of the formula (Va) by the process described above were hiterto unknown. However, they can be prepared by a process in which an amine of the general formula

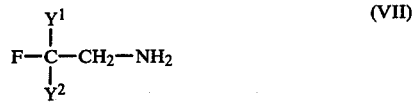

in which
Y$^1$ and Y$^2$ have the meanings given above, is reacted with a carbonyl compound of the general formula

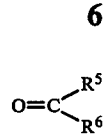

in which
R$^5$ and R$^6$ have the meanings given above, if appropriate in the presence of a diluent (such as pentane, hexane, cyclohexane, chloroform, carbon tetrachloride, benzene, toluene, xylene, chlorobenzene, diethyl ether, tetrahydrofuran or dioxane) at a temperature between −20° C. and +60° C., preferably between 0° C. and +40° C.

Amines of the formula (VII) and carbonyl compounds of the formula (VIII) required as starting materials in the synthesis of the fluorinated azomethines of the formula (VI) by the above process are known and can be prepared by methods which are known in principle (in this context see German Published Specification DOS No. 3,018,030).

1-Methyl-2,2,2-trifluoroethylamine, which is of particular interest as a starting compound, can advantageously be prepared starting from 1,1-difluoropropene, via 1-methyl-2,2,2-trifluoronitroethane and the catalytic hydrogenation thereof, according to the following equation (for the method see: Izvest. Akad. Nauk SSSR, Ser. Khim, 1963, pages 1794 et seq. (English version); and also Tetrahedron 26, pages 5737 to 5743 (1970)):

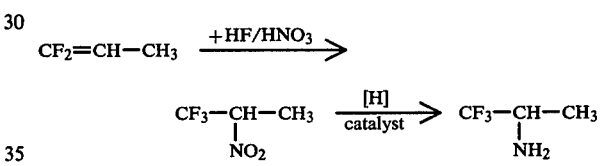

In carrying out the conjugated addition of HF and HNO$_3$ to 1,1-difluoropropene, the nitric acid is preferably employed in an equimolar amount (an excess is also possible); hydrogen fluoride is employed in amounts greater than the stoichiometric amount and serves simultaneously as the solvent. The nitro compound is obtained in yields of up to 86% of theory. In the subsequent catalytic hydrogenation, any of the customary noble metal catalysts (such as Pd or Pt, and also Raney nickel) can be used. Further, reduction can also be carried out using nascent hydrogen, for example with the system Fe/H$^+$—with or without the addition of bases, such as M$_g$CO$_3$ or Na$_2$CO$_3$, as acid acceptors. Suitable solvents or diluents are alcohols (such as methanol or ethanol), ethers (such as diisopropyl ether) and water (see Examples 1 and 2 hereinbelow).

In the two processes according to the present invention for the production of compounds of formulae (I) and (II), respectively, which have been described above, the reaction temperatures can be varied within a certain range. The reaction is carried out in general at a temperature between 0° and 50° C. (preferably between 20° and 45° C.) in the first stage of the process for the production of compounds of formula (I), and in general at a temperature between 50° and 150° C. (preferably between 50° and 110° C.) in the second stage of the process for the production of compounds of formula (I) and in general at a temperature between −10° and +25° C. (preferably between 0° and 20° C.) in the process for the production of compounds of formula (II).

The following general data relating to the molar ratios, diluents, acid-binding agents and working-up applies equally to the process for the production of compounds of formula (I) and the process for the production of formula (II).

In carrying out the processes according to the invention, the starting materials and, if appropriate, the acid-binding agents are employed in about equimolar amounts.

The reactions are preferably carried out in the presence of a diluent. Any of the inert organic solvents are suitable diluents. These include, as preferences, hydrocarbons (such as benzene and xylene), chlorinated hydrocarbons (such as chlorobenzene and carbon tetrachloride), ketones, (such as acetone and methyl ethyl ketone), ethers, (such as tetrahydrofuran and dioxane) and amides (such as dimethylformamide).

Some of the reactions can also be carried out in an aqueous medium. In the case of the reaction of triazines of the formula (II) with alcoholates, the alcohol on which the alcoholate is based can advantageously be used as the diluent.

Any of the customary acid-binding agents can be used as the acid-binding agent. These include, as preferences, the tertiary amines (such as trimethylamine, triethylamine and pyridine), alkali metal hydroxides (such as sodium hydroxide and potassium hydroxide) and also alkali metal carbonates (such as sodium carbonate and potassium carbonate). In the first stage of the process for the production of compounds of formula (I), an equimolar excess of the amine of the formula (III) can also be used as an acid-binding agent.

The working-up and isolation of the reaction products are effected in the customary manner. When water is added to the reaction mixture, the reaction products are generally precipitated in crystalline form if water-miscible solvents have been used.

The active compounds according to the invention influence plant growth and can therefore be used as defoliants, desiccants, agents for destroying broad-leaved plants, germination inhibitors and, especially, as weed-killers. By "weeds" in the broadest sense there are meant plants growing in places where they are not desired.

Whether the compounds according to the invention act as total herbicides or selective herbicides depends essentially on the amount used.

The active compounds according to the present invention may be used, for example, to combat the following plants:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

The active compounds according to the present invention may be used, for example, as selective herbicides in the following cultures:

dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera Oryza, Zea, Triticum, Hordeum, Avena, Secale, Sorghum, Panicum, Saccharum, Ananas, Asparagus and Allium.

However, the use of the active compounds according to the invention is in no way restricted to these genera but also embraces other plants, in the same way.

Depending on the concentrations, the compounds can be used for the total combating of weeds, for example on industrial terrain and railway tracks and on paths and squares with or without trees. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

The compounds according to the invention are active against dicotyledon plants, in particular Sinapis, Chenopodium, Urtica, Stellaria, Galium and Daucus, as well as against monocotyledon plants, in particular millet species. The new active compounds are superior to the known herbicidal triazines particularly in their action against millet species, for example Echinochloa, Digitaria, and Setaria. The active compounds according to the invention can be used selectively in various crops, for example in cereals, cotton and onions. The active compounds are particularly well tolerated by corn; they can therefore particularly advantageously be used as selective corn herbicides, and, owing to their substantially better action in particular against graminaceous weeds of the millet species, they are superior to the previously known corn herbicide atrazine.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations may be produced in known manner, for example by mixing the active compounds with extenders, that is to say liquid or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention as such or in the form of their formulations, can also be used, for combating weeds, as mixtures with known herbicides, for example chloroacetanilides, such as Alachlor or Metolachlor, finished formulations or tank mixing being possible. Mixtures with other known active compounds, such as fungicides, insecticides, acaricides, nematicides, bird repellents, growth factors, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, scattering or dusting.

The active compounds according to the invention can be applied either before or after emergence of the plants. They can also be incorporated into the soil before sowing.

The amount of active compound used can vary within substantial ranges. It depends essentially on the nature of the desired effect. In general, the amounts used are between 0.1 and 10 kg of active compound per ha, preferably between 0.2 and 5 kg/ha.

The present invention also provides herbicidal compositions containing as active ingredient a compound of the present invention in admixture with a solid diluent or carrier or in admixture with a liquid diluent or carrier containing a surface-active agent.

The present invention also provides a method of combating weeds which comprises applying to the weeds, or to a habitat thereof, a compound of the present invention alone or in the form of a composition containing as active ingredient a compound of the present invention in admixture with a diluent or carrier.

The present invention further provides crops protected from damage by weeds by being grown in areas in which immediately prior to and/or during the time of the growing a compound of the present invention was applied alone or in admixture with a diluent or carrier.

It will be seen that the usual methods of providing a harvested crop may be improved by the present invention.

The examples which follow serve to illustrate the invention further. Examples 1 and 2 relating to the production of starting compounds, Example 3 relating to the production of compounds of formula (II) and Example 4 relating to the production of compounds of formula (I).

EXAMPLE 1

(a)

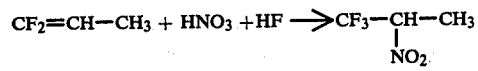

1400 ml of hydrogen fluoride (anhydrous) and 320 g of nitric acid (concentrated) were initially introduced into a stirred steel autoclave and cooled to $-30°$ to $-40°$ C. 390 g (5 mol) of 1,1-difluoropropene were passed in at this temperature. The reaction mixture was allowed to warm up to room temperature, was further stirred for 6 hours, and was then poured onto 2 kg of ice. The aqueous phase was extracted three times with 250 ml of dichloromethane and the combined organic phases were washed neutral with $NaHCO_3$ solution and water, dried with $MgSO_4$ and distilled. After the solvent and first runnings (25 g; boiling range: 43°-98° C.) had been separated off, 615 g ($\triangleq$86% of theory) of 1-methyl-2,2,2-trifluoronitroethane [=1-(trifluoromethyl)nitroethane] were obtained; boiling point 98° to 100° C.; $n_D^{20}$: 1.3380.

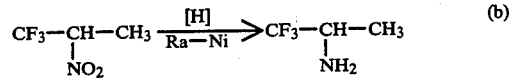
(b)

715 g (5 mols) of 1-methyl-2,2,2-trifluoro-nitroethane in 3 liters of methanol were hydrogenated using 30 g of Raney nickel at a temperature of 30° to 40° C. and a pressure of 40 bar. After the catalyst had been filtered off, the mixture was acidifed with concentrated hydrochloric acid and the volatile constituents were distilled off. 600 g of 50% strength sodium hydroxide solution were added to the residue, and the reaction product was distilled off. 520 g ($\triangleq$92% of theory) of 1-methyl-2,2,2-trifluoro-ethylamine [=1-(trifluoromethyl)-ethylamine] were obtained; boiling point 47° to 48° C.; $n_D^{20}$: 1.3215.

EXAMPLE 2

(a)

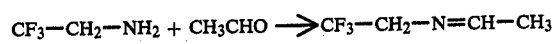

44 g (1 mol) of freshly distilled acetaldehyde were added dropwise to 99 g (1 mol) of 2,2,2-trifluoroethylamine in the course of 60 minutes, while cooling with ice. The mixture was further stirred for 1 hour, 15 g of solid potassium hydroxide were added, and the phases were separated. The organic phase was dried over about 5 g of solid potassium hydroxide and then distilled over a column. After first runnings (20 g; bp: 18°–42° C.) which consisted of unreacted amine and acetaldehyde, 77.5 g (62% of theory) of ethylidene-2,2,2-trifluoroethyl-amine were obtained.

Bp=73° to 74° C.,
$n_D^{20}$=1.3415.

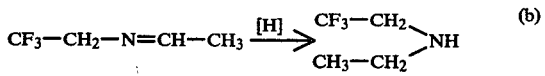

125 g (1 mol) of ethylidene-2,2,2-trifluoroethylamine were dissolved in 250 ml of absolute ethanol, 4 g of platinum on charcoal (5% strength) were added, and hydrogenation was carried out for 90 minutes at 30° C. under a hydrogen pressure of 10 bar. After the catalyst had been filtered off, the mixture was acidified with concentrated hydrochloric acid and concentrated to dryness under reduced pressure. 100 ml of 50% strength aqueous sodium hydroxide solution were added to the resulting product, and the mixture was distilled. 83 g (65% of theory) of 2,2,2-trifluoro-ethyl-N-ethylamine were obtained in this manner.

Bp=61° to 62° C.,
$n_D^{20}$=1.3335.

The following fluorinated amines were also obtained in an analogous manner:

A(a) Intermediate product:
$CF_3-CH_2-N=CH-CH_2CH_3$
Yield: 64% of theory
Bp = 93–95° C.

(b) 2,2,2-trifluoro-ethyl-N—n-propylamine

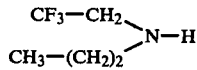

Yield: 66% of theory
$n_D^{20}$ = 1.3462
Bp = 74° C.

B(a) Intermediate product:
$CF_3-CH_2-N=CH-CH_2-CH_2-CH_3$
Yield: 72% of theory
Bp = 116–118° C.

(b) 2,2,2-trifluoro-ethyl-N—n-butylamine

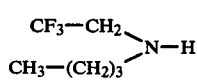

Yield: 72% of theory
$n_D^{20}$ = 1.3590
Bp = 84° C.

PREPARATION OF COMPOUNDS OF FORMULA (II)

EXAMPLE 3

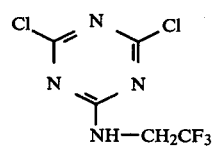

166 g (0.9 mol) of cyanuric chloride were dissolved in 1 liter of warm acetone, the solution was filtered off from the small quantity of insoluble substance, and a solution of 90 g (0.9 mol) of 2,2,2-trifluoroethylamine in 101 g (1.0 mol) of triethylamine was added dropwise at 0° to 5° C., while stirring and cooling with ice. The mixture was stirred for some time, approx. 1 liter of water was added, and the crystals which had formed were filtered off under suction. After the product had been dried, 100 g ($\triangleq$45% of theory) of 2,4-dichloro-6-(2,2,2-trifluoroethylamino)-s-triazine of melting point 115° to 118° C. were obtained.

The compounds of the formula (II) listed in Table 1 below could be prepared in an analogous manner:

TABLE 1

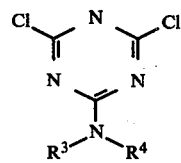

| II | $R^3$ | $R^4$ | Melting point (refractive index $n_D^{20}$) |
|----|-------|-------|---------------------------------------------|
| a | H | $CH_3CF_2CH_2-$ | 104–105° C. |
| b | $CH_3-$ | $CF_3-CH_2-$ | 45–48° C. |
| c | $C_2H_5-$ | $CF_3-CH_2-$ | 70–72° C. |
| d | $C_4H_9-$ | $CF_3-CH_2-$ | (1.4882) |
| e | H | $CF_3-CH_2-CH_2-$ | 76–81° C. |
| f | H | $CF_3-CH(CH_3)-$ | (1.5026) |

EXAMPLE 4

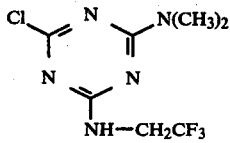

14.8 g (0.06 mol) of 2,4-dichloro-6-(2,2,2-trifluoroethylamino)-s-triazine (prepared as described in Example 3) were dissolved in 100 ml of acetone, and 12 ml of an approximately 45% strength aqueous dimethylamine solution were added dropwise at room temperature. The temperature was kept below 30° C. by cooling with water. The reaction product was precipitated by further addition of water. 14 g (=93% of theory) of 2-chloro-4-dimethylamino-6-(2,2,2-trifluoroethylamino)-s-triazine were obtained; melting point 181° to 184° C.

The compounds of the formula (Ia) listed in Table 2 below were obtained in an analogous manner

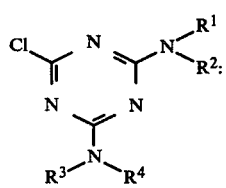

TABLE 2

| Compound No. | $R^1$ | $R^2$ | $R^3$ | $R^4$ | Melting point (refractive index $n_D^{20}$) |
|---|---|---|---|---|---|
| 2 | H | $C_2H_5$ | H | $CF_3CH_2-$ | 244–245° C. |
| 3 | H | $C_3H_5$* | H | $CF_3CH_2-$ | 235–236° C. |
| 4 | H | $n\text{-}C_3H_7$ | H | $CF_3CH_2-$ | 170–171° C. |
| 5 | $C_2H_5$ | $C_2H_5$ | H | $CF_3CH_2-$ | 149° C. |
| 6 | $CH_3$ | $CH_3$ | H | $CH_3CF_2CH_2-$ | 158–160° C. |
| 7 | H | $C_2H_5$ | H | $CH_3CF_2CH_2-$ | 217–218° C. |
| 8 | H | $i\text{-}C_3H_7$ | H | $CH_3CF_2CH_2-$ | 135–139° C. |
| 9 | H | $C_3H_5$* | H | $CH_3CF_2CH_2-$ | 219–220° C. |
| 10 | $C_2H_5$ | $C_2H_5$ | H | $CH_3CF_2CH_2-$ | 119° C. |
| 11 | $C_3H_7$ | $C_3H_7$ | H | $CH_3CF_2CH_2-$ | 115° C. |
| 12 | H | $n\text{-}C_3H_7$ | $CH_3$ | $CF_3CH_2-$ | 129° C. |
| 13 | H | $CH_3$ | $CH_3$ | $CF_3CH_2-$ | 140° C. |
| 14 | $C_2H_5$ | $C_2H_5$ | $CH_3$ | $CF_3CH_2-$ | (1.4998) |
| 15 | $CH_3$ | $CH_3$ | $CH_3$ | $CF_3CH_2-$ | 64° C. |
| 16 | H | $i\text{-}C_3H_7$ | $CH_3$ | $CF_3CH_2-$ | 74–75° C. |
| 17 | H | $C_2H_5$ | $CH_3$ | $CF_3CH_2-$ | 145–147° C. |
| 18 | H | $C_3H_5$* | $CH_3$ | $CF_3CH_2-$ | 118° C. |
| 19 | H | $n\text{-}C_3H_7$ | $C_2H_5$ | $CF_3CH_2-$ | 120–121° C. |
| 20 | H | $CH_3$ | $C_2H_5$ | $CF_3CH_2-$ | 134–137° C. |
| 21 | $C_2H_5$ | $C_2H_5$ | $C_2H_5$ | $CF_3CH_2-$ | (1.4922) |
| 22 | $CH_3$ | $CH_3$ | $C_2H_5$ | $CF_3CH_2-$ | 59° C. |
| 23 | H | $i\text{-}C_3H_7$ | $C_2H_5$ | $CF_3CH_2-$ | 67–68° C. |
| 24 | $C_2H_5$ | $C_2H_5$ | $C_2H_5$ | $CF_3CH_2-$ | 132° C. |
| 25 | H | $C_3H_5$* | $C_2H_5$ | $CF_3CH_2-$ | 116° C. |
| 26 | H | $i\text{-}C_3H_7$ | $C_4H_9$ | $CF_3CH_2-$ | 68–72° C. |
| 27 | H | $C_2H_5$ | $C_4H_9$ | $CF_3CH_2-$ | 126° C. |
| 28 | $C_2H_5$ | $C_2H_5$ | $C_4H_9$ | $CF_3CH_2-$ | (1.4855) |
| 29 | H | $C_3H_5$* | $C_4H_9$ | $CF_3CH_2-$ | 106–107° C. |
| 30 | H | $i\text{-}C_3H_7$ | H | $CF_3-CH(CH_3)-$ | 185–186° C. |
| 31 | H | $C_3H_7$ | H | $CF_3-CH(CH_3)-$ | 122–125° C. |
| 32 | H | $C_2H_5$ | H | $CF_3CH(CH_3)-$ | 148–149° C. |
| 33 | $C_2H_5$ | $C_2H_5$ | H | $CF_3CH(CH_3)-$ | 68–72° C. |
| 34 | H | $C_4H_9$ | H | $CF_3CH(CH_3)-$ | 117–120° C. |
| 35 | H | $CH_3$ | H | $CF_3CH(CH_3)-$ | 150° C. |
| 36 | $CH_3$ | $CH_3$ | H | $CF_3CH(CH_3)-$ | 120–123° C. |
| 37 | H | $t\text{-}C_4H_9$ | H | $CF_3CH(CH_3)-$ | 141–146° C. |
| 38 | H | H | H | $CF_3CH(CH_3)-$ | 135° C. |
| 39 | H | $CH_3$ | H | $CF_3CH_2CH_2-$ | 248–250° C. |
| 40 | $CH_3$ | $CH_3$ | H | $CF_3CH_2CH_2-$ | 200–202° C. |
| 41 | H | $C_2H_5$ | H | $CF_3CH_2CH_2-$ | 215–218° C. |
| 42 | $C_2H_5$ | $C_2H_5$ | H | $CF_3CH_2CH_2-$ | 130–132° C. |
| 43 | H | $n\text{-}C_3H_7$ | H | $CF_3CH_2CH_2-$ | 225–228° C. |
| 44 | H | $C_3H_5$* | H | $CF_3CH_2CH_2-$ | 205° C. |
| 45 | H | $i\text{-}C_4H_9$ | H | $CF_3CH_2CH_2-$ | 216–220° C. |
| 46 | H | $i\text{-}C_4H_9$ | H | $CF_3CH_2CH_2-$ | 141–148° C. |
| 47 | H | $CH_2=CH-CH_2-$ | H | $CF_3CH(CH_3)-$ | 122–125° C. |

TABLE 2-continued

| Compound No. | R$^1$ | R$^2$ | R$^3$ | R$^4$ | Melting point (refractive index n$_D^{20}$) |
|---|---|---|---|---|---|
| 48 | H | C$_2$H$_5$SCH$_2$CH$_2$— | H | CF$_3$CH(CH$_3$)— | 101–104° C. |
| 49 | H | CH$_3$OCH$_2$CH$_2$— | H | CF$_3$CH(CH$_3$)— | 96–99° C. |
| 50 | C$_3$H$_7$— | C$_3$H$_7$— | H | CF$_3$CH(CH$_3$)— | 82–84° C. |
| 51 | i-C$_3$H$_7$— | i-C$_3$H$_7$— | H | CF$_3$CH(CH$_3$)— | (1.4953) |
| 52 | H | C$_2$H$_5$CH(CH$_3$)— | H | CF$_3$CH(CH$_3$)— | 203° C. |
| 53 | H | ClCH$_2$CH$_2$— | H | CF$_3$CH(CH$_3$)— | 142–144° C. |
| 54 | H | i-C$_4$H$_9$— | H | CF$_3$CH(CH$_3$)— | 148–149° C. |
| 55 | H | (CH$_3$)$_3$C—CH$_2$— | H | CF$_3$CH(CH$_3$)— | 152–154° C. |
| 56 | CH$_2$=CH—CH$_2$— | CH$_2$=CH—CH$_2$— | H | CF$_3$CH(CH$_3$)— | 55–60° C. |
| 57 | H | HOCH$_2$CH$_2$— | H | CF$_3$CH(CH$_3$)— | 123–126° C. |
| 58 | H | CH$_3$OCH$_2$CH$_2$CH$_2$— | H | CF$_3$CH(CH$_3$)— | 120–121° C. |
| 59 | H | C$_2$H$_5$C(CH$_3$)$_2$— | H | CF$_3$CH(CH$_3$)— | 160–161° C. |
| 60 | H | C$_2$H$_5$OC(=O)—CH$_2$— | H | CF$_3$CH(CH$_3$)— | 139–141° C. |

*C$_3$H$_5$ = CH$_2$=CH—CH$_2$— (Allyl)

EXAMPLE 35/PREFERRED PROCESS VARIANT

It has proven particularly advantageous to prepare the compound of Example 35, starting from cyanuric chloride, in a "one-pot reaction", in which the intermediate product (see Example 72) is not isolated. In detail the reaction is advantageously carried out as follows:

520 g (2.82 mol) of cyanuric chloride are dissolved in toluene at room temperature; the solution is cooled to 5°–10° C. While stirring 324 g (2.86 mol) of 1-methyl-2,2,2-trifluoro-ethylamine (see Example 73) are added dropwise at 8°–10° C., stirring is continued for a short time (approx. 15 minutes) and a solution of 118 g NaOH/400 ml water is then added at the same temperature.

When the temperature has risen to approx. 15° C. 310 ml of aqueous, 32.5% strength methylamine solution (3.2 mol of CH$_3$NH$_2$) are added at 15°–20° C.

Then the mixture is again subsequently stirred for 15 minutes and 113 g NaOH/300 ml water are then added dropwise at the same temperature.

During this the reaction mixture becomes very pulpy. After stirring for a short time at 25° C. the mixture is acidified with HCl and heated to about 80° C. At this temperature a clear solution forms. The two phases are separated, the hot toluene solution is if necessary filtered to remove small amounts of insoluble matter and is cooled. The product crystallizes in the cold at 10°–15° C. from the toluene solution. The crystals are filtered off, washed with toluene and dried.

Yield:

588 g (=82% of theory) 2-chloro-4-methylamino-6-(1-methyl-2,2,2-trifluoro-ethylamino)-s-triazine of the formula

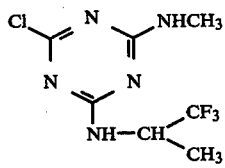

Melting point 149°–150° C.; purity determined by gas chromatography: 99.8%

EXAMPLE 5

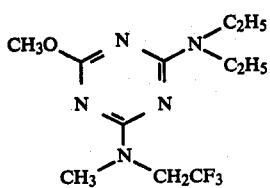
(61)

10.4 g (0.035 mol) of 2-chloro-4-diethylamino-6-(N-methyl-N-2,2,2-trifluoroethylamino)-s-triazine (compound 14 of Table 2) were dissolved in 100 ml of methanol, and 7 ml of a 1N sodium methylate solution were added. The mixture was heated to the boil for 1 hour, methylene chloride was added, the reaction solution was extracted several times by shaking with water, and the methylene chloride phase was concentrated. The reaction product was thus obtained in the form of an oil. Yield 7.6 g (=75% of theory) of 2-methoxy-4-diethylamino-6-(N-methyl-N-2,2,2-trifluoroethylamino)-s-triazine; $n_D^{20}$: 1.4762.

The compounds of the formula Ic listed in Table 3 below were obtained in an analogous manner:

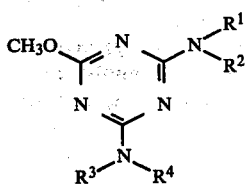
(Ic)

TABLE 3

| Compound No. | $R^1$ | $R^2$ | $R^3$ | $R^4$ | Melting point (refractive index $n_D^{20}$) |
|---|---|---|---|---|---|
| 62 | $C_2H_5$ | $C_2H_5$ | $C_2H_5$ | $CF_3CH_2$— | (1.4754) |
| 63 | H | i-$C_3H_7$ | $CH_3$ | $CF_3CH_2$— | 87–90° C. |
| 64 | H | i-$C_3H_7$ | $C_2H_5$ | $CF_3CH_2$— | 76–77° C. |

EXAMPLE 6

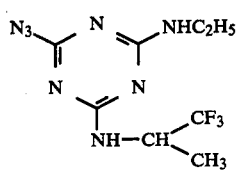
(65)

A solution of 7.8 g (0.029 mol) of 2-chloro-4-ethylamino-6-(1-methyl-2,2,2-trifluoroethyl-amino)-s-triazine (compound 32 of Table 2) and 2 g (0.031 mol) of sodium azide (NaN₃) in 100 ml of dimethylformamide was heated on a boiling water bath for 3 hours. After the reaction mixture had cooled, it was poured into water and the reaction product was filtered off under suction. It was rinsed with water and dried. Yield 7 g (=100% of theory) of 2-azido-4-ethylamino-6-(1-methyl-2,2,2-trifluoroethyl-amino)-s-triazine; melting point 69° to 75° C.

The herbicidal activity of the compounds of this invention is illustrated by the following biotest examples.

In these examples, the compounds according to the present invention are each identified by the number (given in brackets) of the corresponding preparative Example.

EXAMPLE 7

Pre-emergence test
Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the plants was rated in % damage in comparison to the development of the untreated control. The figures denoted: 0%=no action (like untreated control) 100%=total destruction In this test, for example, the following compounds showed an excellent activity: (32) and (35).

EXAMPLE 8

Post-emergence test/greenhouse
Solvent: 5 parts by weight of acetone
Emulsifier: 1 part by weight of alkylarly polyglycol ether To produce a suitable preparation of active compound, 1 part by weight of active compound was mixed with the stated amount of solvent, the stated amount of emulsifier was added and the concentrate was diluted with water to the desired concentration.

Test plants which had a height of 5 to 15 cm were sprayed with the preparation of the active compound in such a way as to apply the amounts of active compound per unit area which are indicated in the table. The concentration of the spray liquor was so chosen that the amounts of active compound shown in the table were applied in 2,000 liters of water/ha. After three weeks, the degree of damage to the plants was rated in % damage in comparison to the development of the untreated control. The figures denoted:
0%=no action (like untreated control)
100%=total destruction In this test, for example, the following compounds showed an excellent activity: (32) and (35).

It will be appreciated that the instant specification and examples are set forth by way of illustration and not limitation, and that various modifications and changes

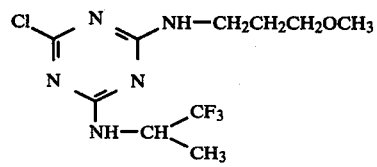

We claim:

1. A fluorine-containing 4,6-diaminotriazine of the formula

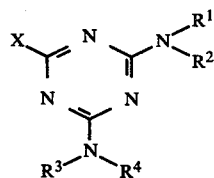

wherein
- X is a chlorine atom, an alkoxy radical having 1 to 4 carbon atoms, an alkylthio radical having 1 to 4 carbon atoms or the azide radical,
- $R^1$, $R^2$ and $R^3$ each independently is a hydrogen atom, an alkyl radical having 1 to 6 carbon atoms or an alkenyl radical having 3 to 6 carbon atoms,
- $R^2$ is, in addition, one of the following aliphatic radicals: ethylthioethyl, methoxyethyl, 2-chloroethyl, 2-hydroxyethyl or ethoxycarbonylmethyl and
- $R^4$ is a fluoroalkyl radical having 1 to 8 carbon atoms and 1 to 9 fluorine atoms or a fluorochloroalkyl radical having 1 to 8 carbon atoms and up to a total of 9 fluorine and chlorine atoms.

2. A compound according to claim 1, wherein such compound is 2-chloro-4-isopropylamino-6-(2,2,2-trifluoroethylamino)-s-triazine of the formula

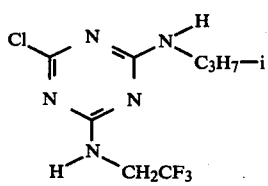

3. A compound according to claim 1, wherein such compound is 2-chloro-4-ethylamino-6-(1-methyl-2,2,2-trifluoroethylamino)-s-triazine of the formula

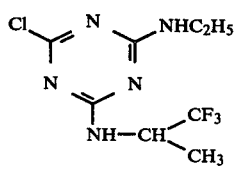

4. A compound according to claim 1, wherein such compound is 2-chloro-4-methylamino-6-(1-methyl-2,2,2-trifluoroethylamino)-s-triazine of the formula

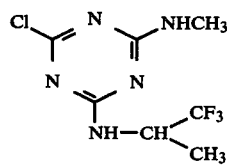

5. A compound according to claim 1, wherein such compound is 2-azido-4-ethylamino-6-(1-methyl-2,2,2-trifluoroethyl-amino)-s-triazine of the formula

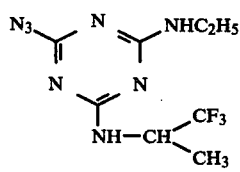

6. A herbicidal composition comprising a herbicidally effective amount of a compound according to claim 1 in admixture with a diluent.

7. A method of combatting weeds which comprises applying to the weeds, or to a habitat thereof, a herbicidally effective amount of a compound according to claim 1.

8. The method according to claim 8, wherein such compound is
- 2-chloro-4-isopropylamino-6-(2,2,2-trifluoroethylamino)-s-triazine,
- 2-chloro-4-ethylamino-6-(1-methyl-2,2,2-trifluoroethylamino)-s-triazine,
- 2-chloro-4-methylamino-6-(1-methyl-2,2,2-trifluoroethylamino)-s-triazine,
- 2-azido-4-ethylamino-6-(1-methyl-2,2,2-trifluoroethylamino)-s-triazine, or
- 2-chloro-4-(3-methoxy-n-propylamino)-6-(1-methyl-2,2,2-trifluoroethylamino)-s-triazine.

9. A compound according to claim 1, wherein such compound is 2-chloro-4-(3-methoxy-n-propylamino)-6-(1-methyl-2,2,2-trifluoroethylamino)-s-triazine of the formula